United States Patent

Maschino et al.

Patent Number: 5,531,778
Date of Patent: Jul. 2, 1996

[54] CIRCUMNEURAL ELECTRODE ASSEMBLY

[75] Inventors: Steven Maschino, Angleton; Ross G. Baker, Jr., Houston, both of Tex.

[73] Assignee: Cyberonics, Inc., Webster, Tex.

[21] Appl. No.: 308,978

[22] Filed: Sep. 20, 1994

[51] Int. Cl.[6] ........................................... A61N 1/05
[52] U.S. Cl. ............................. 607/118; 128/642
[58] Field of Search ...................... 607/115–118, 2, 607/17, 61; 128/642

[56] References Cited

U.S. PATENT DOCUMENTS

| | | | |
|---|---|---|---|
| 3,405,715 | 10/1968 | Hagfors | 128/118 |
| 4,026,300 | 5/1977 | DeLuca et al. | 607/17 |
| 4,156,429 | 5/1979 | Amundson | 607/119 |
| 4,825,871 | 5/1989 | Cansell | 607/2 |
| 4,920,979 | 5/1990 | Bullara | 607/118 |
| 5,215,089 | 6/1993 | Baker, Jr. | 607/118 |
| 5,344,438 | 9/1994 | Testerman et al. | 607/642 |

*Primary Examiner*—Lee S. Cohen
*Assistant Examiner*—Stephen Huang
*Attorney, Agent, or Firm*—Wigman, Cohen, Leitner & Myers

[57] ABSTRACT

An electrode assembly of a lead to be implanted on a patient's nerve includes a flexible electrically insulative carrier of helical configuration, a flexible ribbon electrode secured to the underside of at least a segment of the helical configuration carrier, an elongate conductor for electrical connection to the ribbon electrode, and a flexible conducting spacer electrically connected to the ribbon electrode and to the elongate conductor for separating the latter from the helical configuration while maintaining electrical connection between the two at the distal end of the elongate conductor. The distal end of the conductor projects directly and tangentially from a curved portion of the spacer in a direction substantially parallel to the longitudinal axis of the helical configuration.

8 Claims, 2 Drawing Sheets

CIRCUMNEURAL ELECTRODE ASSEMBLY

BACKGROUND OF THE INVENTION

The present invention relates generally to nerve electrodes, and more particularly to an improved circumneural electrode assembly of added strength and flexibility for implantation on and electrical stimulation of a selected nerve or nerve bundle of a patient.

Circumneural electrodes are generally designed to encompass a portion of a nerve longitudinally to permit electrical stimulation of the nerve. The stimulation may be intended to modulate electrical signals or impulses normally carried by the nerve. Alternatively or additionally, the nerve electrode may be used for sensing electrical signals carried by the nerve. The required installation of the electrode on a nerve for such purposes presents a considerable number of design problems. To provide mechanical stability of the electrode relative to the nerve, and in recognition that the nerve can move relative to the surrounding tissue, a structure which encompasses the nerve is desirable, and provides efficiency in minimizing or optimizing the distance between the stimulating electrode and the nerve body. It is axiomatic, however, that nerves are sensitive and are easily damaged or traumatized by abrasion or stresses caused by subjection to mechanical forces.

Such forces may be attributable to constriction of the nerve by the circumneural electrode, or to pulling or torque transmitted to the electrode (and thus, to the nerve) by a lead wire. Or the nerve may atrophy as a consequence of lack of nutritional fluid exchange owing to the close proximity of the electrode. Cuff electrodes were popular as nerve electrodes at one time, but lost much of their original appeal because they were found to be too stiff—their rigidity often causing nerve damage.

U.S. Pat. No. 4,573,481 ("the '481 patent") discloses an implantable helical electrode assembly in which the configuration is composed of one or more flexible ribbon electrodes each partially embedded in a portion of the peripheral surface of an open helical dielectric support matrix adapted to be threaded or wrapped around a selected nerve or nerve bundle during surgical implantation of the electrode assembly. The resiliency of the assembly allows it to expand in the event of swelling of the nerve. The electrode assembly is utilized to electrically trigger or measure an action potential or to block conduction in nerve tissue.

Such a helical electrode, with its expansion characteristic, allows "one size" to fit a multitude of variations in nerve diameter encountered in different patients at a given nerve stimulation site. It also allows fluid exchange between the helical coils and is mechanically compliant at its ends. However, some difficulty may be experienced in attempting to install the configuration on the patient's nerve, because it is necessary to unravel the helical configuration and then reform it about the nerve. An improvement over the '481 patent electrode design is disclosed in U.S. Pat. No. 4,920,979, in which a flexible electrode-supporting matrix has two oppositely directed helical portions which are centrally joined and have free outer ends. The helical portions extend circumferentially at least one turn and up to as much as about two turns. A thin, flexible conductive ribbon is secured to the inner surface to provide multiple electrodes on one or both portions, with a connecting electrical cable to couple the electrode array to an electronics package intended for stimulation and/or sensing, implanted elsewhere in the body.

In the design of the '979 patent, the central passage through the two oppositely directed helical portions accommodates a pair of pins which extend at an acute angle from the respective closed legs of a tweezer-like installation tool. When the pins are inserted through the central passage and the legs of the tweezers are opened, the helical portions are distorted and spread open so that the assembly can be slipped over the nerve with the two open-sided portions restrained in a direction generally perpendicular to the length of the nerve. When released by withdrawing the pins of the installation tool, the two end portions return to a helical shape to encircle the nerve with their electrode portions conductively contacting the nerve surface. This type of electrode assembly simplifies installation of the electrode and reduces trauma to the nerve during implantation.

Despite the availability of these and other circumneural helical or spiral electrodes, problems remain in the attachment of the lead wire to the electrode assembly. A particular problem lies in attempts to address conflicting design goals of maximizing mechanical strength for fatigue resistance while minimizing spring constant to allow compliance with the nerve and its movement. It is desirable to improve the strength, durability, flexibility and fatigue resistance of the electrode assembly itself, and as well, to improve the mechanical strength of the electrical connection between the lead conductor and the electrode assembly.

FIG. 1 illustrates a lead 10 of a type heretofore available for implantation in the human body for use in nerve stimulation, including a lead body 11 having lead connectors 12 at its proximal end, and a helical or spiral electrode assembly 13 at its distal end. The connectors 12 are designed to mate with female electrical connectors of an implanted generator (not shown) of electrical signals for electrical stimulation of the nerve and/or for sensing the electrical signals carried by the nerve. The lead body 11 typically comprises an MP35N (cobalt chromium alloy) electrical coil conductor with a biocompatible electrically insulative sheath.

As will be described in greater detail with reference to FIGS. 2 and 3 below, the electrode assembly 13 includes one or more single turn platinum spiral electrical stimulation ribbon conductors with a 90% platinum/10% iridium alloy wire reinforcing component in the weld between the conductor coil and the ribbon electrode. The ribbon conductor is molded in a silicone elastomer insulating material so that the conductor portion is bonded to the insulation but exposed at the underside of the spiral. An integral anchor tether 15 is employed to retain the implanted electrode in place without undue flexing, thereby substantially reducing the possibility of fatigue and fracture of the electrode or the weld connection to the conductor coil.

In this prior art design of FIG. 1, the platinum ribbon used for the stimulating electrode surface is heat treated or annealed, which makes the platinum material soft and ductile. These properties make the lead, and especially the ribbon electrode, vulnerable to damage during implantation as a result of excessive manipulation or improper handling. For example, during installation on the nerve, the electrode helix may be overly stretched by the surgeon to leave it in a deformed condition. Deformation of the platinum material for this or any other cause potentially affects its performance and long term reliability as a nerve-stimulating electrode.

For the sake of clarity, certain details of the prior design of the electrode assembly 13 are shown in FIG. 2. The assembly 13 includes an electrode helix consisting of a single turn of platinum ribbon 20 bonded (e.g., molded) to the inner surface of a silicone elastomer helix 21 which continues through one additional turn 22 and 23 at either end of the platinum ribbon 20 to form a three-turn helix in which each of the single end turns is simply an extension of the central elastomer portion to which the ribbon conductor 20 is bonded. The molding process may utilize injection molding or flow molding, or other known techniques, for example. The coil conductor 25 of lead 10 is welded at 27 to ribbon electrode 20 prior to the molding of the ribbon in the silicone elastomer to achieve the helical shape. A silicone sheath 28 covers the entire length of the lead body. A suture 24 runs the length of the helical configuration.

Details of the welded ribbon electrode subassembly 30 of the prior design are illustrated in FIG. 3. The structure is shown prior to being molded into a helical structure, and the silicone insulating material is not shown, for the sake of clarity. The MP35N quadfilar coil conductor 25 has a 0.25 mm outer diameter, and has an end welded at joint 27 to the 0.025 mm thick by 1.0 mm wide annealed platinum (99.95%) ribbon 20, and then formed into a radius bend 36. The ribbon is heat-treated in an alcohol flame except in the area of the weld. Heat-treated platinum is more ductile, but suffers from lower tensile strength and lower fatigue resistance. The ribbon portion is subsequently molded in silicone elastomer. The ribbon has flaps 31, 32 at its ends, and suture holes 34, 35 at the ends at or very near the point at which the flap commences.

Although the tether 15 (FIG. 1) reduces the magnitude of repetitive, albeit small force loads that exist on the lead connection to the electrode after implantation, there remains the possibility of mechanical fatigue at the weld joint 27. Also, the lead body (sheathed coil conductor) should exit from the helical structure above (about 1.25 mm, in the configuration described above) the molded ribbon conductor to avoid interference with the adjacent spiral structure as well as contact with the nerve and resulting abrasions. However, the radius bend 36 of the lead coil conductor 25 tends to exacerbate the problem, by creating a lever action at the weld joint. Also, the welding process itself heat treats the area in the immediate vicinity of the weld, thereby tending to reduce the strength of the weld. The transition zone between the stronger non-heat treated area and the weaker heat treated areas has the potential for fatigue.

It is a principal object of the present invention to provide an improved lead and electrode, or electrode assembly, for nerve stimulation. Consistent with that object, the electrode assembly is configured for relative ease of implantation and reliable retention on the nerve, while providing improved flexibility and mechanical strength and fatigue resistance of the lead/electrode connection relative to nerve electrodes of the prior art.

Another object of the invention is to provide an improved nerve lead and electrode assembly which is configured in a way that avoids abrasion or other damage to the nerve either from the electrode assembly or the lead conductor itself, while assuring good retention and flexibility characteristics.

Yet another object of the invention is to provide an improved lead and electrode assembly for nerve stimulation in which the electrode design minimizes tissue ingrowth at the welded coil region, between the ribbon and elastomer interface.

SUMMARY OF THE INVENTION

The preferred embodiment of a nerve electrode of the present invention has a ribbon conductor portion composed of platinum which is not heat treated or annealed and is therefore stronger than the prior art designs. In addition, the ribbon is thinner to improve both its flexibility and elastic memory. These characteristics allow the electrode to be opened and placed around the nerve during implantation with substantially greater assurance that, upon closing, it will return to its original shape without distortion. In addition, the number of turns of the helix is reduced in the improved design from that of the prior art design described above. In this embodiment, for example, the turn count is reduced from 3 to 2½. This reduction simplifies installation, while maintaining an adequate number of turns for attachment.

Major improvements of the new lead, in addition to non-annealed ribbon conductor, reside in the ribbon electrode assembly and the coil-to-ribbon weld termination. The ribbon assembly improvement includes a ribbon conductor segment composition enhanced by reinforcing the platinum electrode segment, for example with 80% platinum/20% iridium alloy. Both ribbons are 0.013 mm thick—a total thickness of 0.026 mm—identical to the thickness of the prior art design. The use of the 80%/20% Pt/Ir alloy markedly improves the strength of the coil/ribbon weld junction, because the alloy does not suffer a loss of mechanical strength in the weld area.

In addition, the weld junction is improved by welding the conductor coil of the lead directly to the reinforced ribbon. In the previous design, the weld to the platinum ribbon annealed the ribbon at the weld area. That welding process annealed the ribbon directly under the weld, which created three zones of stress concentration. Two were at either end of a non-annealed region about the weld, and the third was directly beneath the weld. The new technique improves the mechanical interlocking of the coil and ribbon structure into the silicone elastomer, which reduces the stress transmitted directly from the coil to the ribbon and prevents separation of the silicone elastomer from inside the welded ribbon area. The weld area is inside a cylinder formed by the ribbon loop, and the silicone elastomer is dropped inside this cylinder. The elastomer undergoes swelling in body fluids, which further increases mechanical stability inside the weld loop and is expected to prevent or to minimize tissue ingrowth into this area, in contradistinction to the prior art design.

In essence, the electrode assembly of a lead to be implanted on a patient's nerve includes a flexible electrically insulative carrier of helical configuration, a flexible ribbon electrode secured to the underside of at least a segment of the helical configuration, an elongate conductor for electrical connection to the ribbon electrode, and a flexible conducting spacer electrically connected to the ribbon electrode and to the elongate conductor for separating the latter from the helical configuration while maintaining electrical connection between the two at the distal end of the elongate conductor. The distal end of the conductor (i.e., the lead) projects directly and tangentially from a curved portion of the spacer in a direction substantially parallel to the longitudinal axis of the helical configuration.

BRIEF DESCRIPTION OF THE DRAWINGS

The above and still further objects, features and attendant advantages of the invention will become apparent from a consideration of the following detailed description of the presently contemplated best mode and method of practicing the invention, and certain preferred embodiments thereof, taken in conjunction with the accompanying drawings, in which.

DETAILED DESCRIPTION OF THE PREFERRED EMBODIMENTS

Figure 1:
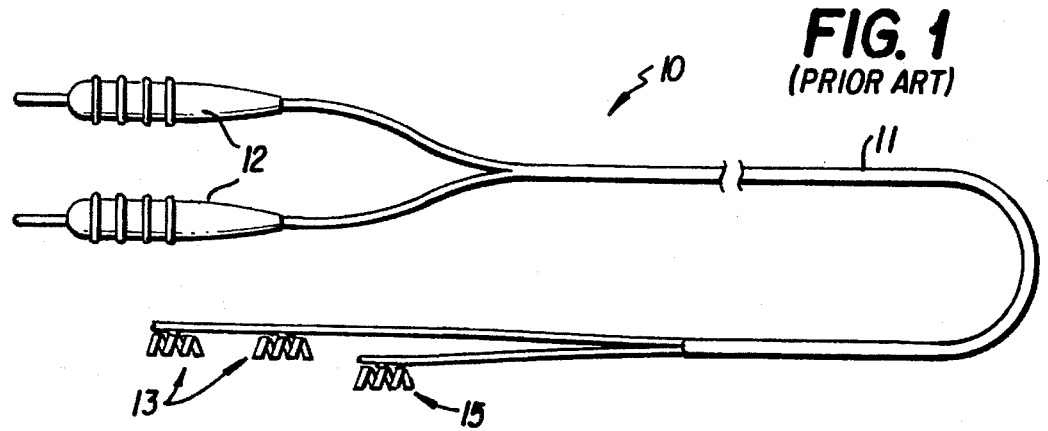
FIG. 1 is a side view of a nerve-stimulating lead with electrode assembly of the prior art.
Figure 2:
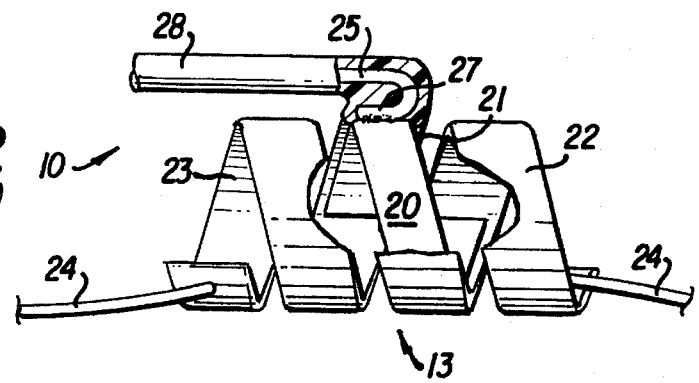
FIGS. 2 and 3 are side and perspective views, respectively, of details of the electrode assembly and subassembly of the lead of FIG. 1.
Figure 3:
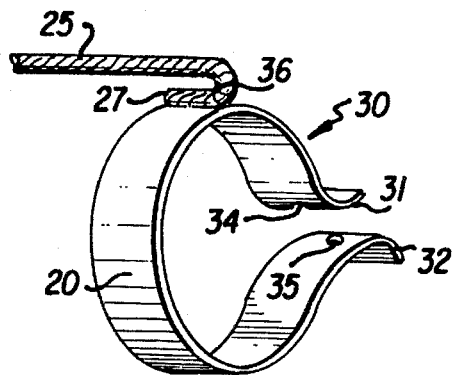

In the design of the preferred embodiment of a spiral electrode assembly 53 according to the invention, illustrated in FIG. 4, the electrode ribbon conductor 60 is molded with silicone elastomer 61 to achieve a helical shape in substantially the same manner as was described with respect to FIG. 2 except as follows. The platinum ribbon helix 60 is substantially one complete turn, band or loop as before, but the shape and composition of a portion of the ribbon 60 is modified as will be described presently with reference to FIG. 5. In the final molded configuration, the silicone elastomer helix 61 extends ¾ of a turn from each end of the elastomer to which the ribbon conductor is molded. More importantly, the MP35N quadfilar coil conductor 65 of 0.25 mm outer diameter is welded for electrical connection to the ribbon conductor 60 in a manner and location to provide the advantages of considerably improved mechanical strength and fatigue resistance of the electrical connection between the conductor coil of the lead and the ribbon electrode assembly.

Figure 4:
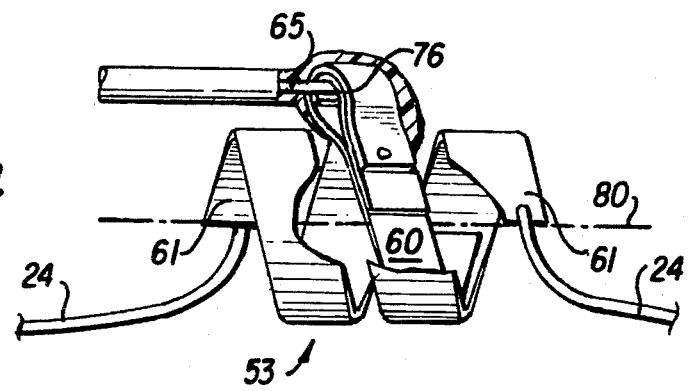
FIGS. 4 and 5 are side and perspective views, respectively, of details of a preferred embodiment of an electrode assembly of a nerve-stimulating lead according to the invention.
Figure 5:
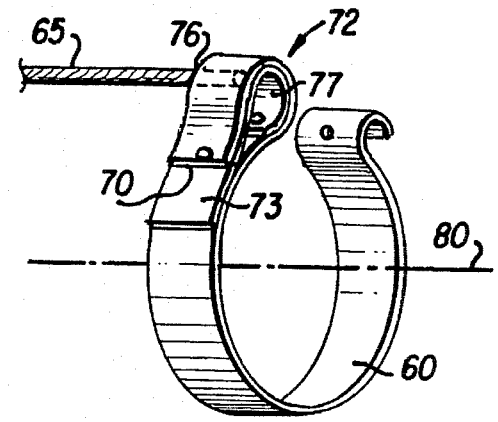

The end loop electrode subassembly of the assembly of FIG. 4 is shown in FIG. 5 without the silicone elastomer insulating material and prior to molding into a helical structure. The major part of the ribbon conductor 60 itself is composed of 99.95% platinum ribbon of 1.0 mm width as before, but with a thickness of 0.013 mm, approximately one-half the thickness of the previous design, in the as-drawn condition (i.e., as a result of the drawing process by which the ribbon is formed). In addition, at one of its ends 70 the ribbon conductor 60 is turned back on itself (i.e., everted) to provide an end loop 72 at which the distal end of coil conductor 65 of the lead is to be welded. In particular, this end loop 72 includes at least a portion to which an electrically conductive reinforcing member 73 is fastened to provide a surface to which the coil conductor is welded.

Preferably, the reinforcing member 73 is another ribbon conductor of substantially the same width and thickness as the main helical electrode 60 but having a composition which is an alloy of 80% platinum and 20% iridium (80% platinum/20% iridium). Thus, the preferred reinforcing ribbon 73 for the main ribbon conductor 60 described above for the configuration of FIG. 4 is a 1.0 mm wide, 0.013 mm thick 80% platinum/20% iridium in the as-drawn condition. This reinforcing ribbon has a length sufficient that when it is fastened to the end portion of the outer surface of the main ribbon conductor it forms a substantial segment of what becomes the inner surface of the end loop 72 when the end 70 of the main ribbon is turned or looped back on itself (everted). The fastening of the two ribbons 73 and 60 is achieved by welding their overlapping surfaces together with the two in juxtaposed alignment.

In the preferred embodiment, the reinforcing ribbon 73 extends beyond the end of the main ribbon 60 so that it may be fastened by welding to the outer surface of the main ribbon to complete (i.e., close) the end loop 72 and to assure that at no point does the end loop exceed the approximate thickness of two layers of ribbon. Before turning the reinforced ribbon conductor (i.e., the now-fastened combination of the main ribbon and overlapping reinforcing ribbon conductors) back on itself and welding the free end to the outer surface of the main ribbon to close the end loop 72, the free distal end of the coil conductor 65 of the lead is resistance spot welded to the reinforced ribbon structure at a point or points along a line 76 tangent to the surface of the reinforced ribbon structure which is to become the inner surface 77 of the end loop 72. This line should be somewhere within a central portion of the end loop in contrast to a position near the closure of the loop, to maintain the aforementioned flexibility, mechanical strength and fatigue resistance of the electrical connection.

Preferably, when fastened to the helical or spiral electrode configuration, the coil conductor 65 at its distal end extends straight from the end loop 72 with an orientation parallel to the longitudinal axis 80 of the electrode assembly as shown in both FIGS. 4 and 5. Thus, the coil conductor 65 extends from the point(s) of connection to the reinforced ribbon conductor somewhat skewed from a direction orthogonal to the ribbon 60, because of the helical configuration of the ribbon in the final electrode assembly. The molding of the ribbon in the silicone elastomer to form the overall electrode assembly at the distal end of the lead is performed after the welding of the coil conductor to make the electrical connection to the ribbon and the welding of the end of the ribbon to close the end loop.

As an alternative, the electrode assembly can be composed of a single ribbon 60, without reinforcement. Also (and preferably, if a single ribbon is used), rather than using a substantially pure platinum flexible ribbon electrode in the electrode assembly, the ribbon 60 may be composed of the same alloy as the reinforcing second flexible ribbon conductor 73, e.g., 80% platinum/20% iridium (not more than approximately 20% iridium), or approximately 90% platinum and the remainder iridium, or both may be composed of iridium oxide, or even other precious metals or their alloys or oxides (such as rhodium).

Figure 6:
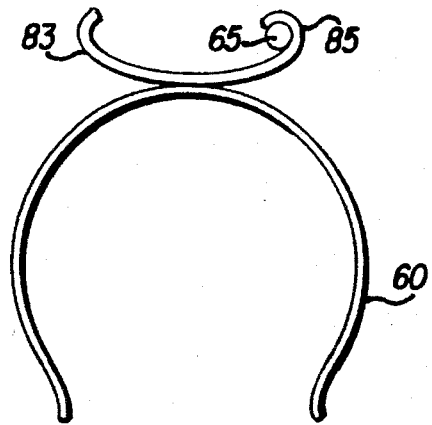
FIGS. 6 and 7 are side views.
Figure 7:
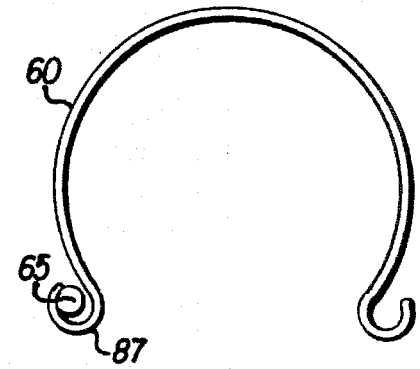
Figure 8:
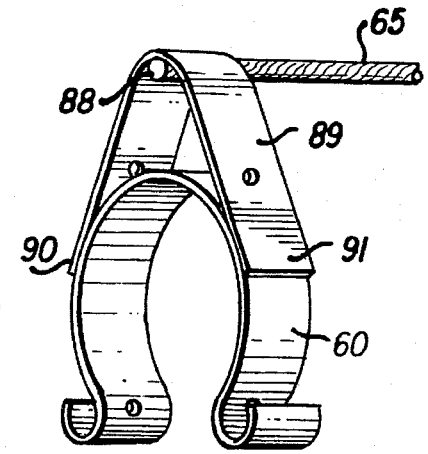
FIG. 8 is a perspective view, of alternative embodiments of a portion of an electrode assembly according to the invention.

Alternative embodiments of portions of improved circumneural electrode assemblies according to the invention are shown in FIGS. 6, 7 and 8. In the embodiment of FIG. 6, shown in a side view, the ribbon conductor electrode 60 is electrically connected by welding to a substantially U-shaped member 83 comprising a second ribbon conductor. The welded connection is preferably made along a line at which the outer surfaces of the two curved members 60 and 83 are tangential to one another. The distal end of coil conductor 65 is welded to the inner surface of an end flap 85 of member 83. The orientation of the conductor relative to the helix formed by conductor 60 in the final electrode assembly is as described above with respect to the embodiment of FIGS. 4 and 5.

In the embodiment of FIG. 7, also shown in a side view, the ribbon conductor electrode 60 has an end flap 87 which is turned backward, similar to the end loop of the embodiment of FIGS. 4 and 5, except that there is no closed loop. The coil conductor 65 is welded at its distal end to what is now the inner surface of this open loop and extends in the manner and with the orientation described above for the other embodiments.

In the embodiment of FIG. 8, shown in perspective view, the distal end of coil conductor 65 is spot welded to the inner surface 88 of an inverted U-shaped conductive member 89 constituting a second ribbon conductor whose ends 90 and 91 are conductively connected by several parallel gap welds to ribbon conductor electrode 60. The inverted U-shaped member or "top hat" acts as a spacer and a mechanically strengthened and fatigue resisting configuration for the lead connection. It may be reinforced in substantially the same manner as was described above for the end loop in the embodiment of FIGS. 4 and 5. The orientation and projection of the coil conductor are as described in that embodiment.

A method of fabricating a nerve electrode according to the invention includes at least the following steps. Initially, a helical electrode is formed which includes a flexible, electrically insulating, ribbon carrier of less than three helical turns with a substantially single turn, flexible, electrically conducting ribbon bonded to and exposed at an underside of a centrally located portion of the carrier. The helical electrode is intended to communicate electrical signals to or from the patient's nerve on which the nerve electrode is to be installed. Then, an electrically conducting lead is provided for transmitting signals communicated to or from the patient's nerve by the helical electrode when installed. Finally, the lead and the helical electrode are electrically connected through an electrically conducting, flexible spacer to separate the lead from the helical electrode in a mechanically damped manner, so as to reduce mechanical fatigue arising from movement between the two.

Although a presently contemplated best mode and method of practicing the invention, including certain presently preferred embodiments thereof, have been described in this specification, it will be apparent to those skilled in the art from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An electrode assembly for a lead to be implanted on a patient's nerve, comprising:

a flexible electrically insulative carrier having a helical configuration with an inner surface, an outer surface and a longitudinal axis, a flexible ribbon electrode secured to the inner surface of at least one segment of the helical configuration, elongate conductor means for electrical connection to said ribbon electrode, said elongate conductor means having a proximal end, a distal end and a longitudinal axis, and flexible conducting spacing means electrically connected to said ribbon electrode and to said elongate conductor means for separating said elongate conductor means from said helical configuration while maintaining electrical connection between said elongate conductor means and said ribbon electrode at said distal end with said distal end projecting directly and tangentially from a curved portion of said flexible conducting spacing means in a direction substantially parallel to the longitudinal axis of the helical configuration; wherein, said flexible ribbon electrode occupies a single substantially complete turn of the helical configuration, and has an inner surface and an outer surface, and said flexible conducting spacing means comprises a curved second ribbon conductor having an inner surface and an outer surface and tangentially connected to the outer surface of said flexible ribbon electrode along one of the inner and outer surfaces of said curved second ribbon conductor.

2. The electrode assembly of claim 1, wherein:

said curved second ribbon conductor is a U-shaped member, said curved second ribbon conductor is connected tangentially at a mid-portion of said outer surface thereof to a mid-portion of said outer surface of said flexible ribbon electrode, and said distal end of said elongate conductor means is electrically connected tangentially to said inner surface of said curved second ribbon conductor at an end of said curved second ribbon conductor.

3. The electrode assembly of claim 1, wherein:

said curved second ribbon conductor is a U-shaped member, wherein the inner surfaces of the two ends of said curved second ribbon conductor are connected tangentially to separated locations along a mid-portion of said outer surface of said flexible ribbon electrode, and said distal end of said elongate conductor means is welded tangentially to said inner surface of said curved second ribbon conductor at a mid-portion of said curved second ribbon conductor.

4. The electrode assembly of claim 3, wherein:

said curved second ribbon conductor includes in a substantial portion thereof an overlapping, third flexible ribbon conductor reinforcing said curved second ribbon conductor in at least said mid-portion thereof in which said distal end is welded.

5. The electrode assembly of claim 4, wherein:

said flexible ribbon electrode is composed of substantially pure platinum, and said second and third flexible ribbon conductors are composed of an alloy of platinum with approximately 20% iridium.

6. The electrode assembly of claim 4, wherein:

said flexible ribbon electrode and said second and third flexible ribbon conductors are each composed of an alloy of platinum with not more than approximately 20% iridium.

7. The electrode assembly of claim 6, wherein:

said flexible ribbon electrode and said second and third flexible ribbon conductors are each composed of an alloy of approximately 90% platinum and remainder iridium.

8. The electrode assembly of claim 4, wherein:

said flexible ribbon electrode and said second and third flexible ribbon conductors are each composed of iridium oxide.

\* \* \* \* \*